US009719901B2

(12) United States Patent
Jackson et al.

(10) Patent No.: US 9,719,901 B2
(45) Date of Patent: Aug. 1, 2017

(54) IMPACT TESTER DEVICE

(71) Applicant: The United States of America as represented by the Administrator of the National Aeronautics and Space Administration, Washington, DC (US)

(72) Inventors: Wade C. Jackson, Yorktown, VA (US); Gregory T. Shanks, Hampton, VA (US)

(73) Assignee: THE UNITED STATES OF AMERICA AS REPRESENTED BY THE ADMINISTRATOR OF THE NATIONAL AERONAUTICS AND SPACE ADMINISTRATION, Washington, DC (US)

(*) Notice: Subject to any disclaimer, the term of this patent is extended or adjusted under 35 U.S.C. 154(b) by 563 days.

(21) Appl. No.: 14/258,382

(22) Filed: Apr. 22, 2014

(65) Prior Publication Data
US 2015/0300933 A1 Oct. 22, 2015

(51) Int. Cl.
G01N 3/307 (2006.01)
G01M 7/08 (2006.01)

(52) U.S. Cl.
CPC ............ G01N 3/307 (2013.01); G01M 7/08 (2013.01)

(58) Field of Classification Search
CPC .................................. G01N 3/307; G01M 7/08
USPC .................................. 73/12.01–12.14, 78–85
See application file for complete search history.

(56) References Cited

U.S. PATENT DOCUMENTS

| 2,130,751 | A | * | 9/1938 | Van Der Meer | E02D 1/022 |
| | | | | | 73/784 |
| 3,407,304 | A | | 10/1968 | Kinard | |
| 3,412,598 | A | | 11/1968 | Webb | |
| 3,605,482 | A | | 9/1971 | Hunes | |
| 4,034,603 | A | * | 7/1977 | Leeb | G01N 3/48 |
| | | | | | 73/12.09 |
| 4,640,120 | A | * | 2/1987 | Garritano | G01N 3/303 |
| | | | | | 73/12.13 |
| 5,739,411 | A | * | 4/1998 | Lee | G01N 3/48 |
| | | | | | 73/12.09 |
| 8,408,042 | B2 | * | 4/2013 | Perrier | G01M 7/08 |
| | | | | | 73/12.01 |
| 9,217,699 | B2 | * | 12/2015 | Klaas | G01N 3/317 |
| 2005/0188744 | A1 | * | 9/2005 | Camio | G01M 7/08 |
| | | | | | 73/12.01 |
| 2010/0192680 | A1 | * | 8/2010 | Brandestini | G01N 3/48 |
| | | | | | 73/82 |
| 2010/0300177 | A1 | * | 12/2010 | Schwarz | G01N 3/307 |
| | | | | | 73/12.05 |
| 2010/0307258 | A1 | * | 12/2010 | Brandestini | G01N 3/307 |
| | | | | | 73/803 |

* cited by examiner

Primary Examiner — Hezron E Williams
Assistant Examiner — Marrit Eyassu
(74) Attorney, Agent, or Firm — Andrea A. Warmbier

(57) ABSTRACT

Systems and methods for testing an impact response of a material and/or structure to one or more impacts of known magnitude. The systems and methods include a portable impactor device for imparting an impact force on a surface of an engineered structure, wherein the portable impactor device has an adjustable orientation such that an impact may be delivered as an angle ranging from +90° to −90° relative to a horizontal plane. Additionally, the portable impactor device described may be utilized to test an impact response of one or more surface areas of a full-scale prototype structure.

14 Claims, 8 Drawing Sheets

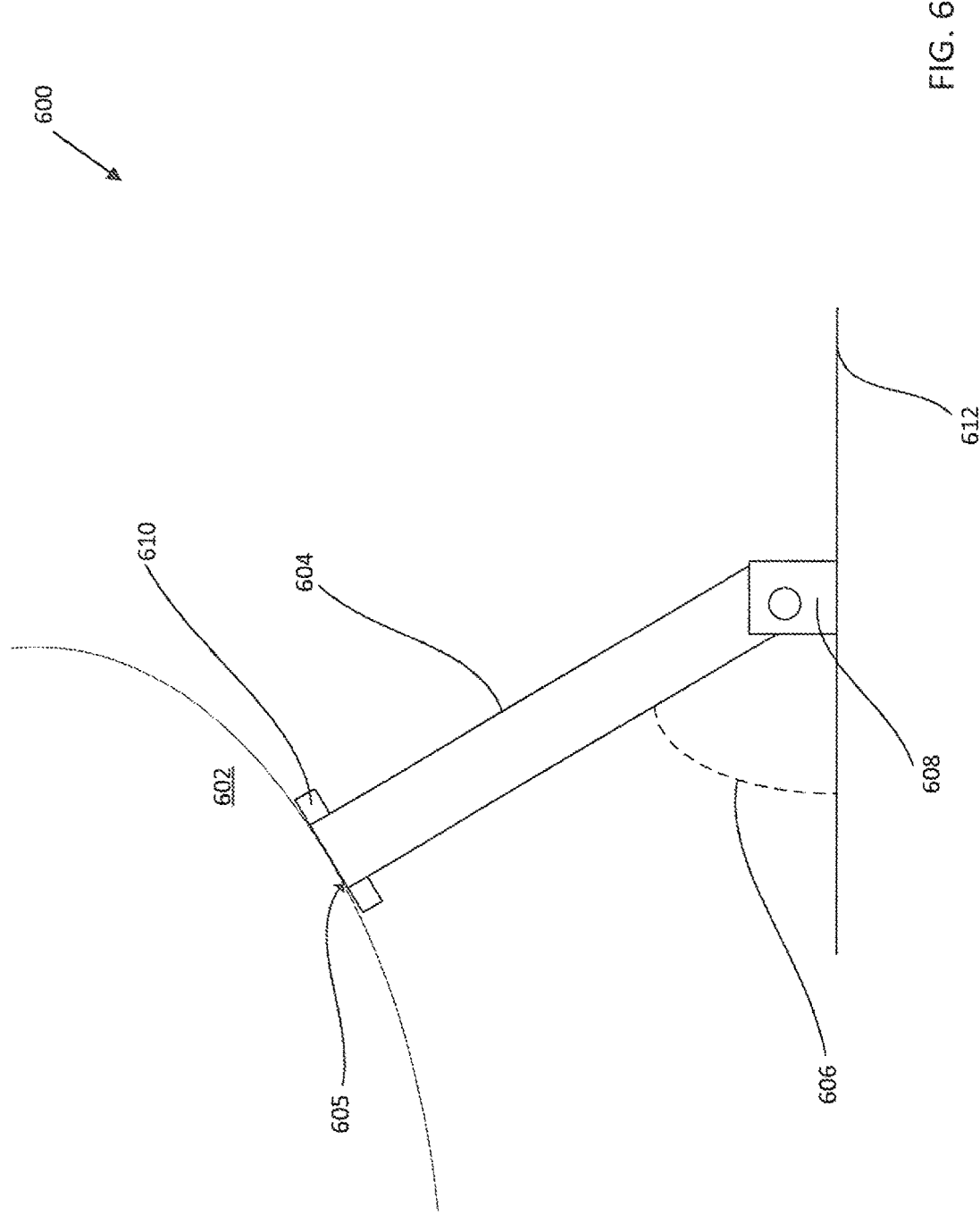

IMPACT TESTER DEVICE

STATEMENT REGARDING FEDERALLY SPONSORED RESEARCH OR DEVELOPMENT

The invention described herein was made by employees of the United States Government and may be manufactured and used by or for the Government of the United States of America for governmental purposes without the payment of any royalties thereon or therefore.

BACKGROUND OF THE INVENTION

Testing is commonly performed to evaluate a response of a material to an impact. Such testing is of particular importance when the material is to be used as part of a structural element of an engineered device, whereby impact testing may be used to determine that the material is capable of withstanding one or more impacts of a known force or energy without catastrophically failing and/or being damaged beyond a tolerable level.

In one example, an impact test simulates one or more incidental and/or intentional impacts of a material by a projectile. Specifically, an impact test may simulate a force of impact on a composite material to be used in the construction of an aircraft fuselage, wherein the simulated impact forces may model a real world impact that may result from a dropped tool, among others. Those of ordinary skill in the art, however, will readily understand various different impact scenarios that may be simulated with an impact test of an engineering material.

Currently, impact testing is performed on test specimens of a given material. For example, a composite material to be used in the construction of an aircraft fuselage may undergo impact testing in a laboratory environment, and wherein the test specimen of the composite material (otherwise referred to as a "coupon") may measure, for example, 100×150 mm. As such, current impact testing devices drop known masses under the force of gravity onto test specimens. This methodology, however, presents multiple limitations. For example, a small test specimen of an engineering material may behave differently to that of a completed structure constructed using the same engineering material, when impacted. Specifically, a test specimen may transform less kinetic energy from an impact into elastic deformation than that of a larger engineered structure. Additionally, a vibrational response of the material may differ significantly in a complete structure from that of a test specimen as a result of complex vibrational modes set up in a full-scale structure. Accordingly, predicting an impact response of a full-scale structure constructed using a specific material may be difficult when using current impact testing methodology.

BRIEF SUMMARY OF THE INVENTION

One or more of the above-mentioned needs in the art are satisfied by aspects described herein. According to one aspect, an impact tester device may have a tube with a first end and a second end, the first end having a first opening approximately equal in size to a bore of the tube, and a second end having a second opening measuring less than the bore of the tube. Further, the device may have a projectile releasably coupled to an interior wall of the tube by a pin, the projectile further having an impactor tip. The device may further have a cylindrical compression block positioned within the tube between the projectile and the second end of the tube. The device may have a linear actuator coupled to the cylindrical compression block, and configured to move through the second opening in the tube and an axial direction to urge the cylindrical compression block in an axial direction along the tube. Further, the device may have a coil spring sandwiched between the projectile and the cylindrical compression block, wherein upon actuation of the linear actuator rod, the coil spring is compressed against the projectile by the compression block. Upon removal of the pin, projectile may move in an axial direction towards the first opening of the tube, imparting a portion of the kinetic energy of the projectile on a testing surface.

According to one aspect, a unitary device may comprise a tube having a first end with a first opening, and a second end with a second opening. The device may further comprise a projectile, and a compressor device configured to pressurize a gas within a pressure chamber formed between the projectile and the second end of the tube. The device may be further configured to urge the projectile in axial direction towards the first opening, upon release of the projectile from a releasable coupling of the projectile to the tube. In this way, movement of the projectile in the axial direction may be utilized to impart a portion of the kinetic energy of the projectile onto a test surface.

In yet another aspect, a portable impactor device may comprise a tube, a load cell sandwiched between an impactor and in a pusher end of a projectile, and a coil spring, configured to be compressed between a linear actuator and the pusher end of the projectile. The device may further comprise an optical sensor configured to detect to optical flags attached to the projectile. Further, the device may comprise a non-transitory computer-readable medium comprising computer-executable instructions to be executed by a processor to perform a calculation of a force of impact of the projectile against a test surface from data received from the impact load cell, and a calculation of a speed and/or kinetic energy of the projectile just prior to impact the test surface from data received from the optical sensor.

These and other features, advantages, and objects of the present invention will be further understood and appreciated by those skilled in the art by reference to the following specification, claims, and appended drawings.

BRIEF DESCRIPTION OF THE SEVERAL VIEWS OF THE DRAWINGS

FIG. 6 schematically depicts an impactor device testing an impact response of a test surface.

DETAILED DESCRIPTION OF THE INVENTION

Aspects of this disclosure relate to systems and methods for testing an impact response of a material and/or structure to one or more impacts of known magnitude. In particular, the systems and methods described herein include a portable impactor device for imparting an impact force onto a surface of an engineered structure, wherein the portable impactor device has an adjustable orientation such that an impact may be delivered at an angle ranging from +90° to −90° relative to a horizontal plane. Additionally, the portable impactor device described herein may be utilized to test an impact response of one or more surface areas of a full-scale prototype structure.

In the following description of the various embodiments, reference is made to the accompanying drawings, which form a part hereof, and in which is shown by way of illustration various embodiments in which aspects of the disclosure may be practiced. It is to be understood that other embodiments may be utilized and structural and functional modifications may be made without departing from the scope and spirit of the present disclosure.

Figure 1A:
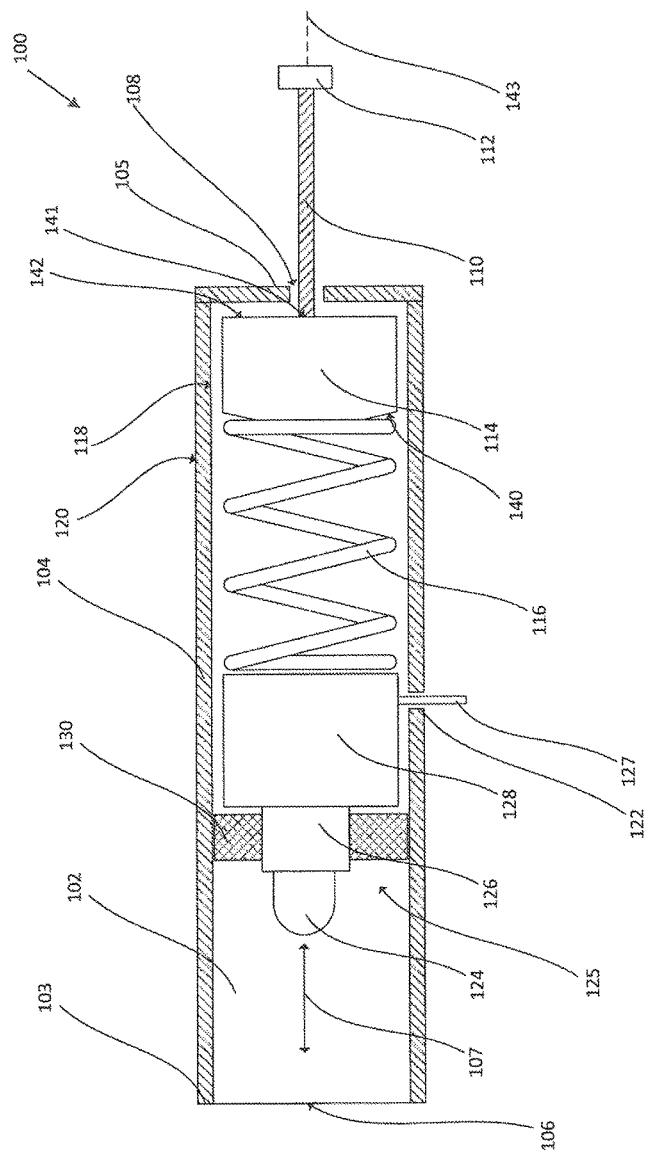
FIGS. 1A-1B schematically depict a portable impactor device according to one example embodiment.

FIG. 1A schematically depicts a portable impactor device 100, otherwise referred to as an impact tester device. In one example, impactor device 100 may be configured to impart a known impact force onto a surface area of a material to be tested. In response to an impact imparted by device 100, one or more hardness and/or strength characteristics of the material may be quantitatively and/or qualitatively observed and/or recorded. In particular, impactor device 100 comprises a tube 102 having a sidewall 104, an interior wall 118, and an exterior wall 120. Tube 102 further comprises a first end 103 having a first opening 106, and a second end 105 having a second opening 108. A linear actuator rod 110 may be configured to translate through the second opening 108 in an axial direction, as indicated by arrow 107. Further, the linear actuator rod 110 comprises a linear actuator interface 112, wherein upon actuation of the linear actuator interface 112, the linear actuator rod 110 translates into/out from the second opening 108. Compression block 114 may be configured with a first end 140, and a second end 142, wherein said second end 142 may be coupled to the first end 141 of the linear actuator rod 110.

In one embodiment, linear actuator rod 110 comprises a threaded rod configured to interface with threads on the second opening 108. Accordingly, in one implementation, actuation of the linear actuator interface 112 comprises rotating the interface 112 about a central axis 143 using, among others, a wrench tool. In another embodiment, linear actuator interface 112 may be actuated by an electronic actuator, such as an electronic motor, among others. Accordingly, in one example, upon actuation of linear actuator interface 112, said threaded linear actuator rod 110 translates in the axial direction 107 relative to the threaded second opening 108.

In one embodiment, the first end 141 of the linear actuator rod 110 may be rigidly coupled to the second end 142 of compression block 114. In another example, the first end 141 of the linear actuator rod 110 may be rotatably coupled to the second end 142 of compression block 114 such that linear actuator rod 110 may rotate about a central axis 143 without rotation of compression block 114. Specifically, in one embodiment, linear actuator rod 110 may be rotatably coupled to the second end 142 of compression block 114 by a bearing, wherein said bearing facilitates rotation of linear actuator rod 110 about a central axis 143 without rotation of compression block 114.

Device 100 further comprises a projectile 125, wherein said projectile 125 includes an impactor tip 124, an impactor load cell 126, and an impactor mass 128. In one example, said projectile 125 may be removably coupled to the interior wall 118 of tube 102 through a sidewall opening 122, and by a pin 127. Furthermore, projectile 125 may include an annular spacer element 130, wherein said annular spacer element 130 may be configured to center the projectile 125 within tube 102. In another embodiment, annular spacer element 130 may comprise one or more low friction and/or lubricating materials (e.g. graphite, among others) such that the annular spacer element 130 may be configured to slide along the interior wall 118 of tube 102. In one embodiment, impact load cell 126 may comprise any load cell known to those of ordinary skill in the art, and configured to output a signal indicative of a force sensed by said load cell device 126. As such, a force sensed by load cell device 126 may correspond to an impact force of impactor tip 124 against a test surface (test surface not shown in FIG. 1A, see exemplary test surface 605 from FIG. 6).

In one embodiment, impactor mass 128 may comprise an interchangeable mass having a known value. Accordingly, in one embodiment, impactor mass 128 may have a mass ranging from approximately 1 kg to approximately 5 kg, among others.

Sandwiched between the first end 140 of compression block 114 and projectile 125 may be a coil spring 116, wherein said coil spring 116 has a known spring constant. In one example, a spring constant (k) coil spring 116 may have a value of 5.7 kN/m. In another example, coil spring 116 may have a spring constant in a range from approximately 5 kN/m-7 kN/m, among others.

Those of ordinary skill in the art will understand that any one or more elements of device 100 may be constructed using any suitable material having strength and/or hardness characteristics suitable for withstanding one or more forces generated during one or more impact tests. As such, any of the aforementioned elements of device 100 may comprise a metal, an alloy, a ceramic, a composite, a polymer, a fiber-reinforced material, a wood, or any other natural or synthetic material known to those of ordinary skill in the art.

In one embodiment, impactor tip 124 comprises a hemispherical indenter with a diameter of approximately 1 cm-5 cm. In one implementation, impactor tip 124 comprises one or more steel materials. In another implementation, impactor tip 124 comprises a pyramid shape, conical shape, a cube (square shape), or any other geometry.

In one embodiment, compression block 114 comprises a first end 140 having a conical shape configured to center coil spring 116 within tube 102. Accordingly, in one embodiment, upon actuation of linear actuator rod 110, compression block 114 may be urged along said axial direction 107 towards projectile 125, wherein said projectile 125 may be releasably coupled to the sidewall 104 of tube 102 by pin 127. As such, translation of compression block 114 towards projectile 125 compresses coil spring 116. In one example, FIG. 1A depicts coil spring 116 in an uncompressed state, while FIG. 1B depicts said coil spring 116 in a compressed state.

Figure 1B:
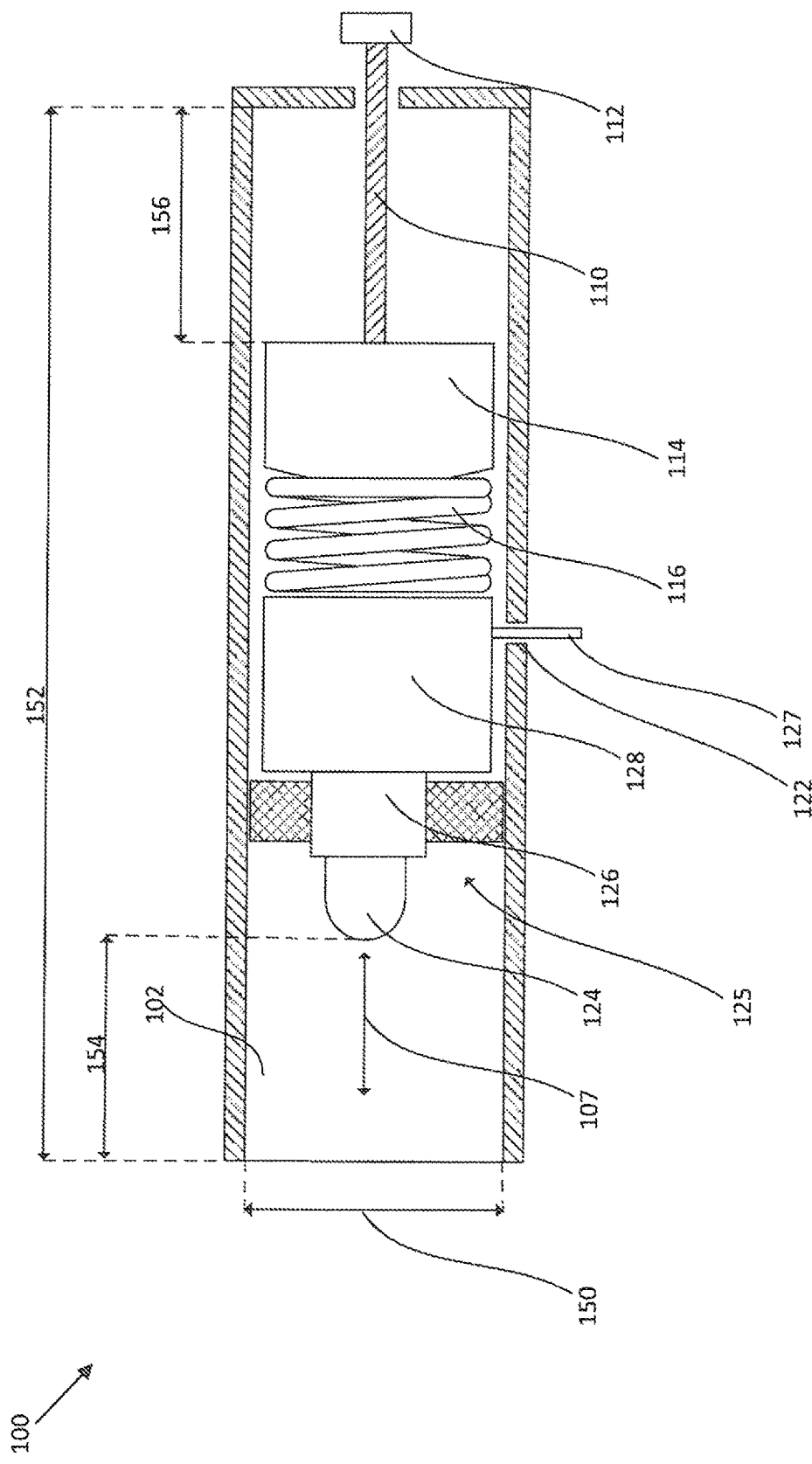

In one embodiment, and as depicted in FIG. 1B, tube 102 has a length 152, wherein said length 152 may range from between approximately 0.2 m and approximately 3 m, among others. In one example tube 102 has a bore 150, wherein bore 150 may measure between approximately 3 cm and approximately 15 cm, among others. In one example, coil spring 116 may be compressed to a known compression distance 156, wherein compression distance 156 corresponds to a distance traveled by linear actuator rod 110 from that position depicted in FIG. 1A with the coil spring 116 in an uncompressed state. In one example, compression distance 156 depicted in FIG. 1B may be a maximum compression distance, wherein a compression distance may be infinitely adjustable between the depicted maximum compression distance 156 and the uncompressed state depicted in FIG. 1A using linear actuator rod 110. Those of ordinary skill in the art will understand that a spring potential energy stored in the compressed coil spring 116 from FIG. 1B may be represented by the equation:

$$E = \tfrac{1}{2}kx^2 \qquad \text{(Equation 1)}$$

Returning to Equation 1: k is a spring constant (N/m), and x is a compression distance (m). In one embodiment, compression distance x corresponds to compression distance 156 from FIG. 1B.

In one embodiment, upon removal of pin 127 from sidewall 104 of tube 102, projectile 125 may be urged along axial direction 107 towards the first end 103 of tube 102 by a spring force resulting from compression of coil spring 116. In this way, the spring potential energy (represented by Equation 1), may be partially transformed into kinetic energy of projectile 125. Accordingly, the energy of projectile 125 is represented by the equation:

$$E = \tfrac{1}{2}kx^2 - mg[a\,\mathrm{Sin}(\alpha)] \qquad \text{(Equation 2)}$$

Returning to Equation 2: k is a spring constant (N/m), x is a compression distance (m), m is a mass of projectile 125 (kg), g is the acceleration due to gravity (g=9.81 m/s^2) a is a linear distance traveled by projectile 125 along tube 102 (m), and α is an angle of tube 102 relative to the horizontal plane (deg) (see angle 606 relative to horizontal plane 612 from FIG. 6). Furthermore, it is noted that Equation 2 assumes that friction is negligible.

In one example, projectile 125 travels distance 154 along the axial direction 107 of tube 102 before impactor tip 124 impacts a test surface (not shown). In one implementation, device 100 may be configured to impart an impact energy of between approximately 3 J and approximately 60 J on a testing surface (not shown).

Figure 2:
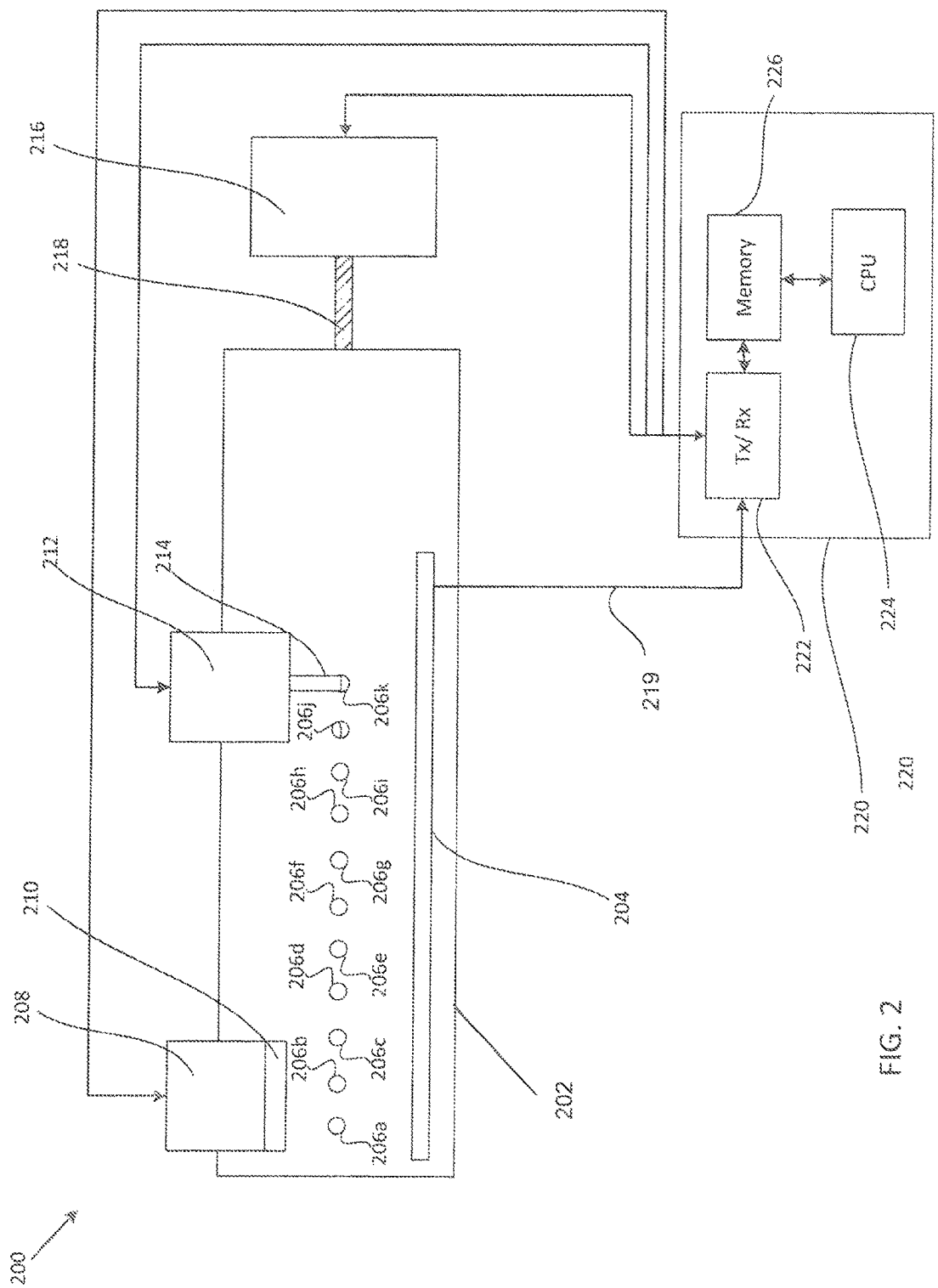
FIG. 2 schematically depicts a portable impactor device according to another example implementation.

FIG. 2 schematically depicts an impactor device 200. In particular, impactor device 200 comprises a tube 202, which may be similar to tube 102 from FIG. 1A, said tube 202 further comprising a plurality of openings 206a-206k, a slot 204, and a window 210. In one example, openings 206a-206k may be spaced apart to allow pin 214 to releasably couple a projectile, such as projectile 125 from FIG. 1A, to a sidewall, such as sidewall 104, of tube 202 at different locations along axial length of tube 202. In this way, openings 206a-206k may allow for variable compression distances of a spring, such as coil spring 116 from FIG. 1A.

In one embodiment, window 210 may be configured to allow an optical sensor 208 to detect one or more flags (otherwise referred to as optical indicators, or indicia) on a projectile, such as projectile 125 from FIG. 1A. Accordingly, those of ordinary skill in the art will recognize various optical sensors that may be utilized with sensor 208, without departing from the scope of this disclosure. Accordingly, in one specific example, optical sensor 208 may be utilized to output a signal indicative of two detections of two optical flag elements attached to a projectile, such as projectile 125 from FIG. 1A.

In one implementation, pin 214 may be actuated using an electronic actuator 212. As such, actuation of pin 214 may release a projectile, such as projectile 125, from a releasable coupling to an interior wall (e.g. interior wall 118) of tube 202. In one example, electronic actuator 212 may comprise any known actuator type, including, among others, a solenoid actuator. In another example, pin 214 may be actuated to manually release a projectile, such as projectile 125, using, among others, a pull cord.

In one implementation, linear actuator rod 218 may be configured to compress the coil spring, such as coil spring 116 from FIG. 1A. Accordingly, linear actuator rod 218 may be actuated using electronic actuator 216, wherein electronic actuator 216 may comprise any actuator known to those of ordinary skill in the art. For example, electronic actuator 216 may comprise an electric motor, or a solenoid actuator.

In one example, impact load cell wire 219 may be configured to connect an impact load cell, such as impact load cell 126 from FIG. 1A, to a computer device, such as computer device 220. Accordingly, in one example, tube 202 may be configured with a slot 204 Slot 204 may be configured to allow impact load cell wire 219 to travel along the axial length of tube 202. As such, wire 219 may travel along slot 204 as the projectile 125 is being urged towards the first end 103, as described in relation to FIG. 1A.

In one implementation, computer device 220 may be configured to send and/or receive electronic instructions to one or more of an impact load cell, such as impact load cell 126, electronic actuator 212, electronic actuator 216, and/or optical sensor 208. Accordingly, computer device 220 may be configured with a transceiver 222, a memory 226, and a processor 224. Those of ordinary skill in the art will understand that various additional components may be included in computer device 220 including, among others, a user interface. Furthermore, those of ordinary skill in the art will understand that transceiver 222 may comprise any hardware suitable for facilitating networking communication. As such, transceiver 222 may communicate with one or more of impact load cell 126, optical sensor 208, electronic actuator 212, and/or electronic actuator 216 by a wired or wireless means, or combinations thereof. Furthermore, transceiver 222 may be configured to communicate using any communication protocol known to those of ordinary skill the art.

Memory 226 may comprise a volatile and/or a persistent form of memory of any known type. As such, memory 226 may be considered a non-transitory computer-readable medium comprising computer-executable instructions that may be executed by processor 224. In one example, memory 226 may, among others, be a ROM, a RAM, a hard disk drive, or a solid state drive, or combinations thereof. Furthermore, processor 224 may comprise one or more processing cores, and may be a dedicated, or a general-purpose processor.

In one example, processor 224 may execute instructions to receive a signal from an impact load cell, such as impact load cell 126, and process the received signal data to calculate a force of impact of the projectile against a test surface (not shown). In another example, processor 224 may execute instructions to receive a signal from optical sensor 208, and calculate a kinetic energy of projectile 125 prior to impact of a test surface (not shown). In yet another example, processor 224 may execute instructions to actuate pin 214 using electronic actuator 212, and/or actuate linear actuator rod 218 using electronic actuator 216.

Figure 3A:
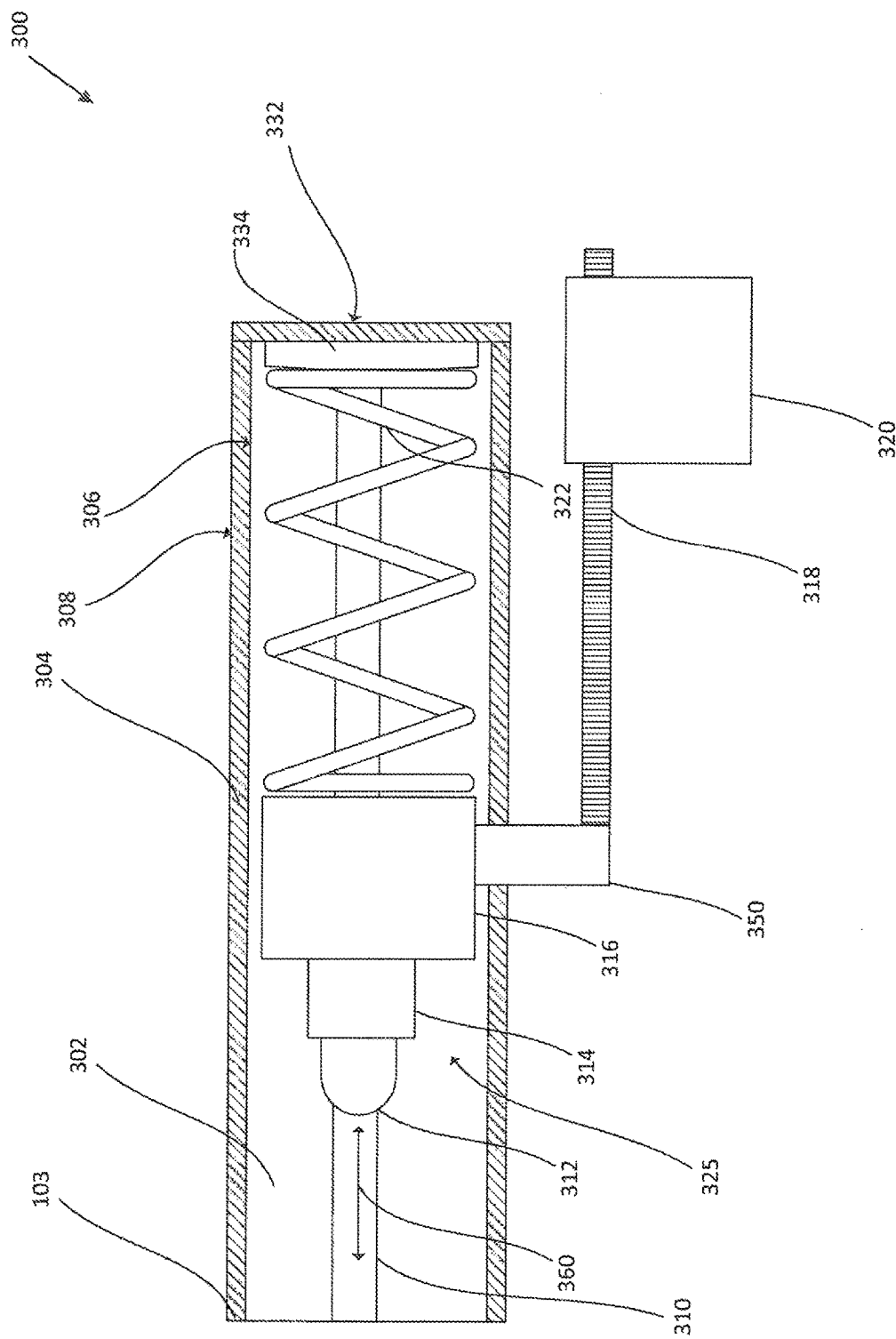
FIGS. 3A-3B schematically depict a portable impactor device according to yet another example implementation.

FIG. 3A schematically depicts an impactor device 300. In one example, impactor device 300 may be similar to devices 100 and/or 200, and include a tube 302, which may be similar to tube 102 from FIG. 1A, and having a sidewall 304, an interior wall 306, and an exterior wall 308. Similarly to device 100, device 300 comprises a coil spring 322, and a projectile 325 having an impactor tip 312, an impact load cell 314, and an impactor mass 316. Those ordinary skill in the art will understand the one or more components depicted in FIG. 3A may be omitted, without departing from the scope of this disclosure. For example, impact load cell 314 may not be utilized, and impactor tip 312 may be directly coupled to impactor mass 316. Furthermore, one or more components labeled in FIG. 3A may be constructed as unitary components.

In one example, the coil spring 322 may be sandwiched between the impactor mass 360 and a compression block 334. Accordingly, in one implementation, linear actuator 318 may be configured to compress coil spring 322 by pulling the impactor mass 316 towards compression block 334 using electronic motor 320, and wherein linear actuator 318 may be connected to impactor mass 316 by bracket 350. In one example, linear actuator 318 comprises a rack gear configured to engage with a pinion gear (not shown) within an electronic motor 320.

Figure 3B:
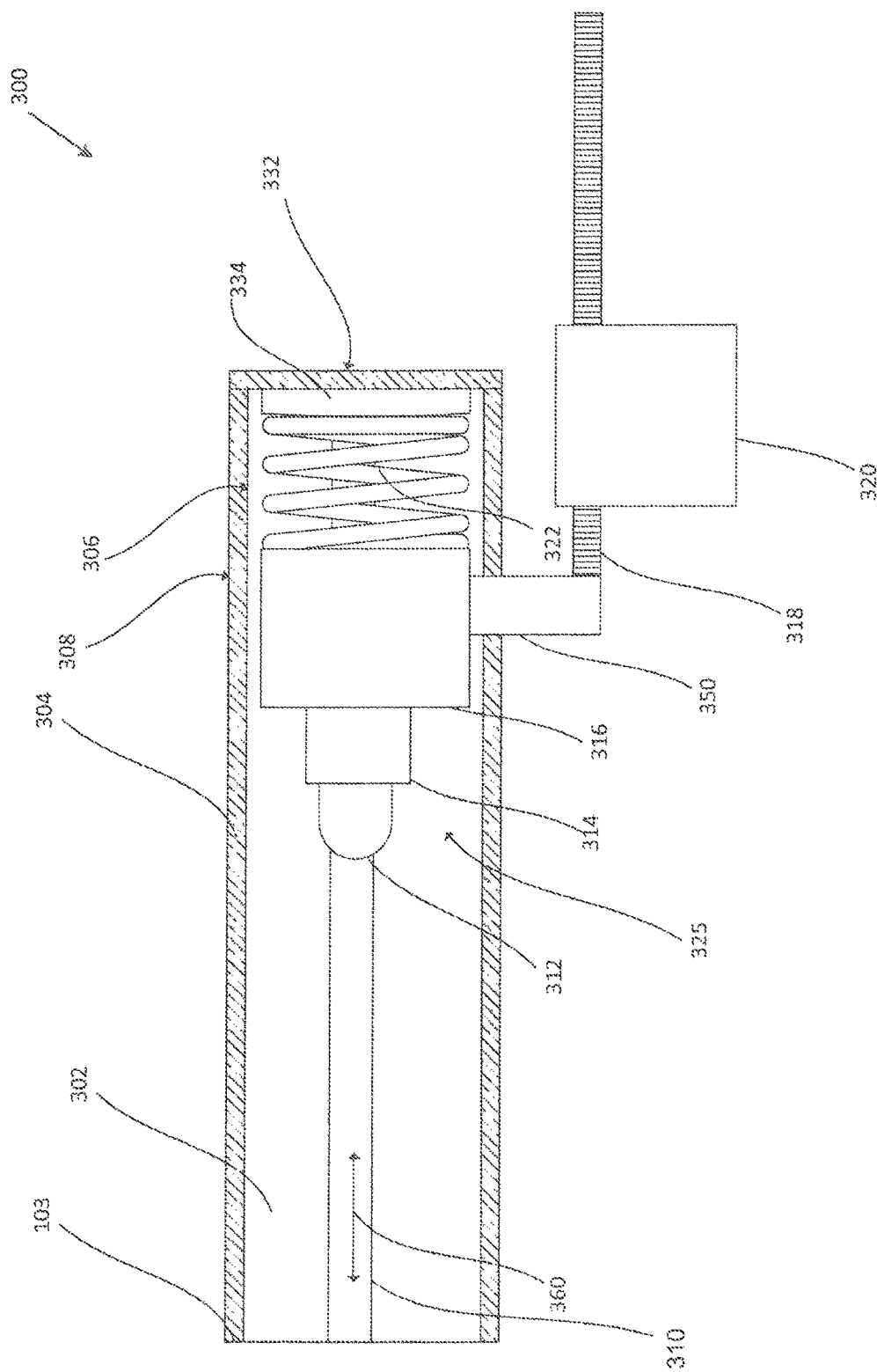

In one implementation, FIG. 3A depicts impactor device 300 having a coil spring 322 in an uncompressed state. Turning to FIG. 3B, coil spring 322 is depicted in a compressed state. In this way, the linear actuator 318 and electronic motor 320 are configured to hold impactor mass 316 (in addition to impactor tip 312 and impact load cell 314) in a position with coil spring 322 in a compressed position. In one example, electronic motor 320 may be configured to selectively disengage from linear actuator 318, thereby allowing coil spring 322 to expand, urging impactor mass 316 to translate in an axial direction (indicated by arrow 360) towards the first end 330 of tube 302. In this way, impactor tip 312, upon reaching the first end 330, may impart a portion of its kinetic energy onto a test surface, such as test surface 605 from FIG. 6.

In one example, projectile 325 may be configured to be aligned with a keyway 310 within tube 302 such that keyway 310 may be configured to receive a key on impactor 325 (not shown) to ensure that projectile 325 maintains a proper orientation within tube 302. In another example, device 300, and in particular, tube 302 may be configured with a linear bearing configured to allow projectile 325 to move in an axial direction 360 through tube 302, wherein said linear bearing may comprise any linear bearing configuration known to those of ordinary skill in the art.

Figure 4:
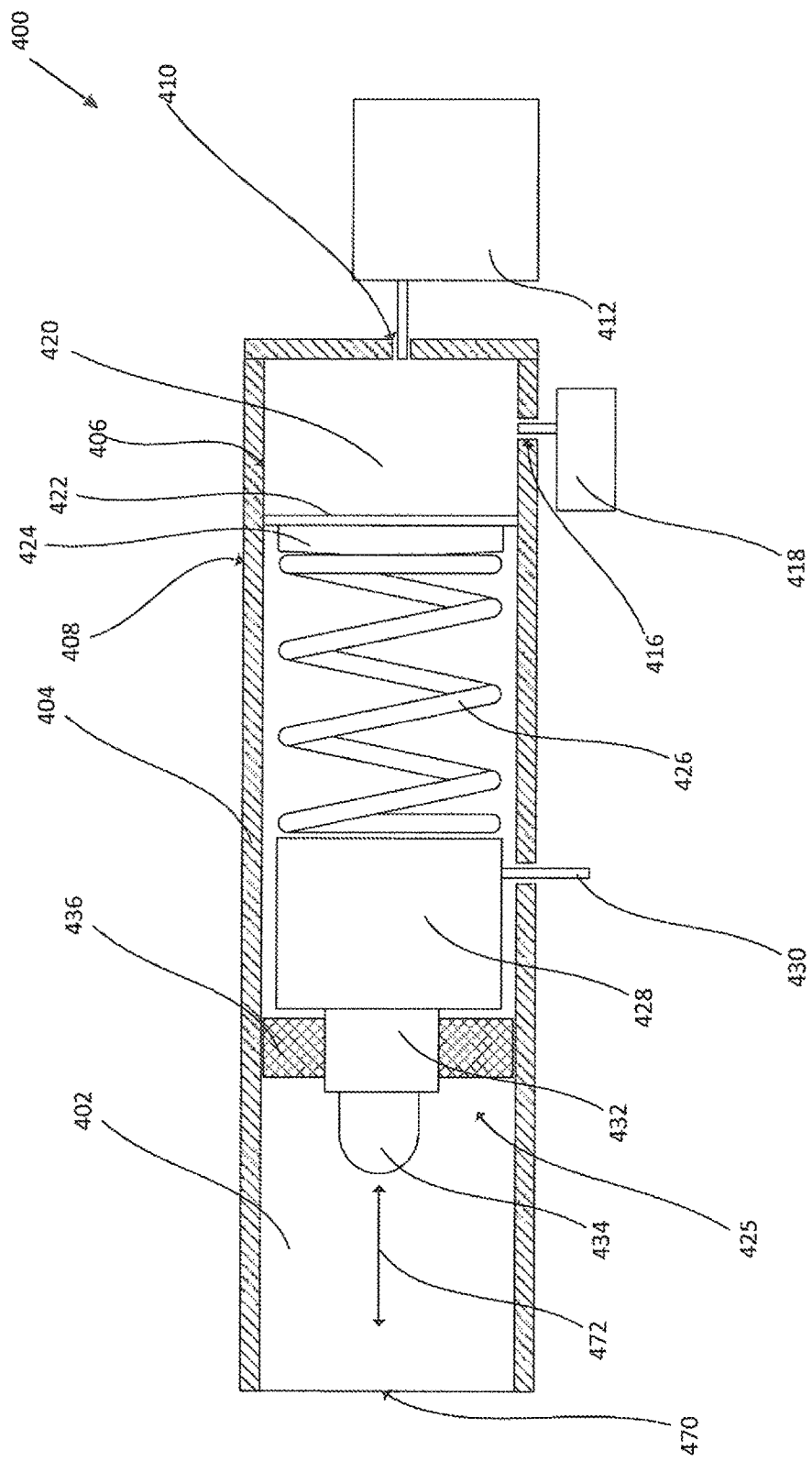
FIG. 4 schematically depicts an alternative implementation of an impactor device.

FIG. 4 schematically depicts an impactor device 400, wherein impactor device 400 may be similar to device 100 from FIG. 1A. As such, impactor device 400 may comprise a tube 402, a sidewall 404, an internal wall 406, and an external wall 408. Further, impactor device 400 may comprise a projectile 425 having an impactor tip 434, an impact load cell 432, an impactor mass 428, and an annular spacer element 436 configured to center projectile 425 within tube 402.

Projectile 425 may be releasably coupled to the internal wall 406 of tube 402 by pin 430, and similar to the releasable coupling of projectile 125 to interior wall 118 in FIG. 1A. Furthermore, coil spring 426 may be sandwiched between projectile 425 and compression block 424, wherein compression block 424 may be configured to compress coil spring 426 by translating along an axial direction of tube 402 (indicated by arrow 472), towards opening 470. In one implementation, compression block 424 may be urged towards opening 470 by increasing a gas pressure within pressure chamber 420. As such, gasket 422 may be coupled to compression block 424, and configured to seal pressure chamber 420, while allowing pressure chamber 420 to increase in volume in response to an increasing gas pressure within said chamber 420. In this way, compression block 424 and gasket 422 may move in an axial direction 472 towards opening 470 upon application of an increased pressure within pressure chamber 420, thereby compressing spring 426 against impactor mass 428. In this way, compression block 424 may be referred to as a piston, and gasket 422 may be referred to as a piston ring. In one example, a pressure of an inert gas within pressure chamber 420 may be augmented using a compressor device 412 connected through inlet 410 via a tube 414. Those ordinary skill in the art will understand that any compressor technology may be utilized in compressor 412 without departing from the scope of this disclosure. Furthermore, those of ordinary skill in the art will understand that any gas may be utilized within pressure chamber 420, such as, among others, air, oxygen, and/or nitrogen. Additionally or alternatively, pressure chamber 420 may pressurize a liquid or a mixture of a liquid and gas, among others. In one implementation, chamber 420 may comprise an opening 416 through which a pressure sensor 418 may monitor a gas/liquid/mixture pressure within pressure chamber 420. As such, pressure sensor 418 may be configured to output an electronic signal indicative of a pressure within pressure chamber 420.

In one example, upon release of pin 430, spring 426 may impart a portion of stored spring energy onto projectile 425. In one implementation, upon release of pin 430, compression block 424 may move in the axial direction 472 towards opening 470, thereby transferring pressure energy from the compressed fluid within chamber 420 to the projectile 425. In another example, upon release of pin 430, compression block 424 may be translate towards opening 470.

In one example, upon compression of coil spring 426 by compression block 424 in response to an increased pressure within pressure chamber 420, projectile 425 may be released from a coupling to the internal wall 406 of tube 402 by removing pin 430, thereby urging projectile 425 to translate along the axial length of tube 402 in the axial direction 472 towards opening 470. In this way, by monitoring a pressure level within pressure chamber 420 using pressure sensor 418, a kinetic energy of projectile 425 may be controlled. In another example, an energy of the projectile 425 may be measured just prior to impact of impactor tip 434 with a test surface. As such, a velocity of projectile 435 may be measured by an optical sensor, such as optical sensor 208 from FIG. 2, and used to calculate a kinetic energy of projectile 425 using a known mass of projectile 425.

Figure 5:
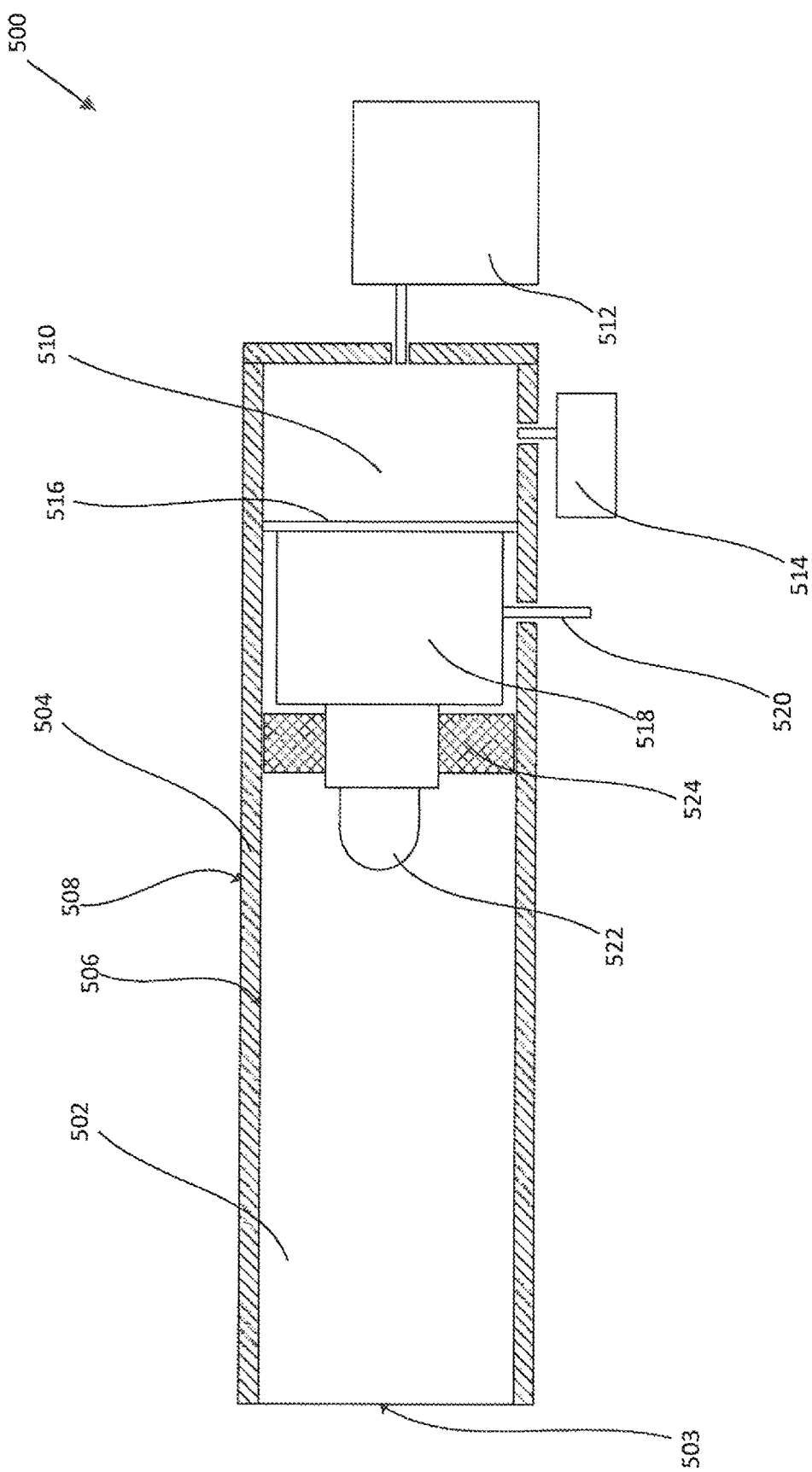
FIG. 5 schematically depicts another alternative implementation of an impactor device.

FIG. 5 schematically depicts an impactor device 500 similar to device 400 from FIG. 4. In particular, device 500 comprises a tube 502 having a sidewall 504, an internal wall 506, and an external wall 508. A projectile 525 may be configured to translate within tube 502, said projectile comprising an impactor tip 522, an impactor mass 518, and having an annular spacer element 524. Projectile 525 maybe releasably coupled to the internal sidewall of tube 502 by pin 520. Additionally, impactor mass 518 may be coupled to a gasket 516, wherein gasket 516 separates projectile 525 from pressure chamber 510.

In one example, pressure chamber 510 may be pressurized with a gas, a liquid, or combinations thereof, using compressor 512. Similarly to pressure sensor 418 from FIG. 4, pressure sensor 514 may be utilized to monitor the pressure level within pressure chamber 510. As such, upon pressurization of pressure chamber 510 using compressor 512, projectile 525 may be released from its coupling to internal wall 506, thereby urging projectile 525 to translate in an axial direction through tube 502 towards opening 503. As such, projectile 525 may be utilized to impart a portion of its kinetic energy onto a test surface, such as test surface 605 from FIG. 6, wherein said kinetic energy results from pressure energy of a gas and/or liquid within pressure chamber 510.

FIG. 6 schematically depicts an impactor system 600. In particular, system 600 includes an impactor device 604, wherein device 604 may be utilized to test an impact response of a structure 602. In one example, impactor device 604 may be similar to one or more of devices 100, 200, 300, 400, and/or 500. In particular, impactor device 604 may be angled at an angle 606 to a horizontal plane 612. As such, angle 606 may be range from approximately +90° to approximately −90°. Accordingly, in one example, impactor device 604 may be held at angle 606 relative to horizontal plane 612 by clamp device 608. Those ordinary skill in the art will understand that any clamp structure may be utilized to orient impactor device 604 an angle ranging from approximately +90° to approximately −90° relative to horizontal plane 612.

In one implementation, impactor device 604 may be configured to impart a portion of the kinetic energy of a projectile, such as projectile 125 from FIG. 1A, onto structure 602. In particular, impactor device 604 may be configured to impact a test surface 605 of structure 602. In one implementation, impactor device 604 may be located at test surface 605 by a locator block 610, wherein locator block 610 may be configured to be removably coupled to the test surface 605, and comprise a bracket for aligning the first end (103) of impactor device 604 at the test surface 605.

What is claimed is:

1. An impact tester device comprising:
   a tube having a first end and a second end, the first end of the tube having a first opening approximately equal in size to a bore of the tube, and the second end of the tube having a second opening measuring less than the bore of the tube;
   a projectile having an impactor tip positioned within the bore of the tube proximate to the first end of the tube;
   a pin moveable relative to the tube, the pin being releasably coupled to the projectile;
   a moveable compression block having a first end and a second end, the compression block positioned within the bore of the tube between the projectile and the second end of the tube;
   a linear actuator rod having a first end, a second end, and an axial length, the first end of the linear actuator rod coupled to the compression block, the linear actuator rod configured to translate through the second opening in the tube in an axial direction; and
   a coil spring positioned between the projectile and the first end of the compression block, the coil spring having a first end engaged with the projectile and a second end engaged with the compression block,
   wherein movement of the linear actuator rod toward the projectile causes; the compression block to move in the axial direction along the tube toward the projectile thereby compressing the coil spring between the compression block and the projectile, wherein engagement of the pin holds the projectile stationary within the tube during the compression of the coil spring,
   wherein upon movement of the pin relative to the tube, stored spring energy in the compressed coil spring is converted into kinetic energy to move the projectile along the axial length of the tube towards the first end of the tube, and
   wherein upon reaching the first end of the tube, the impactor tip of the projectile imparts a portion of the kinetic energy of the projectile on a testing surface in contact with the first end of the tube to test a response of the testing surface to an impact.

2. The device of claim 1, wherein the projectile further comprises:
   an impact load cell, configured to output a signal indicative of a force of impact of the impactor tip against the testing surface in contact with the second end of the tube.

3. The device of claim 2, comprising:
   a slot in a portion of a sidewall of the tube along the axial length of the tube, configured to allow for wired communication between the impact load cell and a processor device external to the tube, wherein a wire connecting the load cell and the processor device is configured to travel along the slot as the projectile travels along the axial length of the tube.

4. The device of claim 1, wherein the projectile further comprises:
   an interchangeable impactor mass, configured to allow for variable impact energies.

5. The device of claim 4, wherein the interchangeable impactor mass has a mass of approximately 1 kg to approximately 5 kg.

6. The device of claim 1, further comprising: a tube clamp, configured to orient the tube at an angle between +90° and −90° relative to a horizontal plane.

7. The device of claim 1, further comprising:
   an opening in a sidewall of the tube, configured to receive an optical sensor, wherein the optical sensor is configured output a signal indicative of two detections of two optical flag elements attached to the projectile.

8. The device of claim 1, further comprising:
   an annular spacer element positioned around the projectile, configured to center the projectile in the tube and slide along the tube.

9. The device of claim 1, wherein a spring constant of the coil spring is known, and wherein the coil spring is compressed by a measurable compression displacement by the linear actuator rod such that a stored spring energy in the compressed coil spring is measurable.

10. The device of claim 1, further comprising: a locator block configured to be removably coupled to the testing surface, and having a bracket for aligning the first end of the tube with the testing surface.

11. The device of claim 1, wherein the device is configured to impart an energy of between approximately 3 J and approximately 60 J on the testing surface.

12. The device of claim 1, wherein the linear actuator rod is a threaded rod, and the second opening is a threaded opening configured to receive one or more screw threads of the linear actuator.

13. The device of claim 1, wherein the linear actuator rod is configured to be actuated using an electric motor.

14. The device of claim 1, wherein:
   the pin is configured to release the projectile using an electronic actuator device;
   the projectile further includes an impact load cell, configured to output a signal indicative of a force of impact of the impact tip against the testing surface in contact with the second end of the tube;
   the projectile further includes an interchangeable impactor mass, configured to allow for variable impact energies;
   a spring constant of the coil spring is known, and wherein the coil spring is compressed by a measurable compression displacement by the linear actuator rod such that a stored spring energy in the compressed coil spring is measurable;
   the device is configured to impart an energy of between approximately 3 J and approximately 60 on the testing surface;
   the interchangeable impactor mass has a mass of approximately 1 kg to approximately 5 kg;
   the linear actuator rod is a threaded rod, and the second opening is a threaded opening configured to receive one or more screw threads of the linear actuator;

the linear actuator rod is configured to be actuated using an electric motor; and the device further comprises;

a tube clamp, configured to orient the tube at an angle between +90° and −90° relative to a horizontal plane;

an opening in a sidewall of the tube, configured to receive an optical sensor, wherein the optical sensor is configured output a signal indicative of two detections of two optical flag elements attached to the projectile;

an annular spacer element positioned around the projectile, configured to center the projectile in the tube and slide along the tube;

a slot in a portion of a sidewall of the tube along the axial length of the tube, configured to allow for wired communication between the impact load cell and a processor device external to the tube, wherein a wire connecting the load cell and the processor device is configured to travel along the slot as the projectile travels along the axial length of the tube; and a locator block configured to be removably coupled to the testing surface, and having a bracket for aligning the first end of the tube with the testing surface.

\* \* \* \* \*